(12) United States Patent
Ho et al.

(10) Patent No.: US 10,155,968 B2
(45) Date of Patent: Dec. 18, 2018

(54) FATTY ACID PRODUCTION IN CELL-FREE SYSTEMS

(71) Applicant: The Regents of the University of California, Oakland, CA (US)

(72) Inventors: Chih-Ming Ho, Los Angeles, CA (US); Yitong Zhao, Los Angeles, CA (US); James C. Liao, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/909,016

(22) PCT Filed: Jul. 29, 2014

(86) PCT No.: PCT/US2014/048681
§ 371 (c)(1),
(2) Date: Jan. 29, 2016

(87) PCT Pub. No.: WO2015/017445
PCT Pub. Date: Feb. 5, 2015

(65) Prior Publication Data
US 2016/0201096 A1    Jul. 14, 2016

Related U.S. Application Data

(60) Provisional application No. 61/859,701, filed on Jul. 29, 2013.

(51) Int. Cl.
*C12P 7/64* (2006.01)
*C12N 1/06* (2006.01)
*C12N 1/12* (2006.01)

(52) U.S. Cl.
CPC .............. *C12P 7/6409* (2013.01); *C12N 1/06* (2013.01); *C12N 1/066* (2013.01); *C12N 1/12* (2013.01); *C12P 7/6427* (2013.01); *C12P 7/6445* (2013.01); *C12P 7/6463* (2013.01)

(58) Field of Classification Search
None
See application file for complete search history.

(56) References Cited

U.S. PATENT DOCUMENTS

| 8,313,647 | B2 | 11/2012 | Kale |
| 8,486,672 | B2 | 7/2013 | Yoshida |
| 2010/0028962 | A1 | 2/2010 | Hu |
| 2011/0009655 | A1* | 1/2011 | Ochiai ................ C12N 9/1025 554/224 |
| 2012/0088011 | A1 | 4/2012 | Thomas |

FOREIGN PATENT DOCUMENTS

| WO | 2008155410 A1 | 12/2008 |
| WO | 2010000416 A1 | 1/2010 |
| WO | WO2012010969 | * 1/2012 |

OTHER PUBLICATIONS

Inoue et al. Phytochemistry (1994), 36(5), 1203-1207.*
Zhang et al. Biomass and Bioenergy (2011), 35(5), 1710-1715.*
Ioki et al. Bioresour Technol. Apr. 2012;109:271-6. Epub Nov. 26, 2011.*
Handayania, N.A., et al., "Potential Production of Polyunsaturated Fatty Acids from Microalgae," Open Access Scientific Reports 1(2):1-4, 2012.
International Search Report and Written Opinion dated Nov. 25, 2014, issued in corresponding International Application No. PCT/US2014/048681, filed Jul. 29, 2014, 10 pages.

* cited by examiner

*Primary Examiner* — Christian L Fronda
(74) *Attorney, Agent, or Firm* — Christensen O'Connor Johnson Kindness PLLC

(57) ABSTRACT

The present invention is directed to methods, compositions, and systems for the production of fatty acids (FAs). Specifically, the disclosed methods, compositions, and systems incorporate algal cell lysates, providing a cell-free environment that generates high levels of FAs for extended periods of time with the addition of liquid media and a carbon source.

11 Claims, 14 Drawing Sheets

FATTY ACID PRODUCTION IN CELL-FREE SYSTEMS

CROSS REFERENCE TO RELATED APPLICATION

This application claims the benefit of U.S. Provisional Application No. 61/859,701, filed Jul. 29, 2013, which is incorporated herein by reference in its entirety.

STATEMENT OF GOVERNMENT LICENSE RIGHTS

This invention was made with Government support under Grant No. CMMI-0751621, awarded by the National Science Foundation. The Government has certain rights in this invention.

FIELD OF THE DISCLOSURE

The present disclosure generally relates to methods and compositions for fatty acid production in cell-free systems.

BACKGROUND

Fatty acids (FAs) have a great variety of uses, including as supplements for human nutrition and health, as ingredients in cosmetic treatments, and as precursors to biofuels such as biodiesel. Considering the ability to readily convert FAs into useful biofuels, especially as an alternative to the extraction and processing of traditional fossil fuels, there is a demand for efficient production of FAs at industrial scales. Currently, large quantities of FAs for this purpose are produced from the hydrolysis of waste vegetable oil. Additional research efforts have addressed FA production in cell cultures, including the use of algae and bacteria, such as *E. coli*, to produce FAs. Various methods to enhance FA production include the application of genetic engineering and biomedical engineering approaches. However, cell-based FA production requires maintenance of various culture parameters over time to maintain cell viability and to optimize production, which increases overall cost.

Accordingly, a need remains for the efficient, scalable production of FAs that is not reliant on maintenance of culture conditions for cell viability.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides a composition comprising an algal cell lysate, liquid medium, and an organic carbon source. The composition is useful for the production of fatty acids.

In another aspect, the present disclosure provides a method for generating fatty acids, comprising providing an organic carbon source to an algal cell lysate, providing a liquid environment to the algal cell lysate, and maintaining the system for sufficient time to permit elongation of fatty acids.

In some embodiments, the liquid environment is sufficient to permit mixing of the carbon source with the lysate.

In another aspect, the present disclosure provides a system that incorporates the disclosed compositions and methods.

DESCRIPTION OF THE DRAWINGS

The foregoing aspects and many of the attendant advantages of the disclosed methods will become more readily appreciated as the same become better understood by reference to the following detailed description, when taken in conjunction with the accompanying drawings, wherein:

FIG. 3A illustrates the Nile Red fluorescent emission profile of samples from the cell-free system and a regular *B. braunii* culture system at day 5. FIG. 3B illustrates the Nile Red fluorescent emission profile of samples from the cell-free system and a regular *B. braunii* culture system at day 28;

FIG. 4A illustrates calibration by oleic acid. FIG. 4B illustrates calibration by linolenic acid;

FIG. 6A illustrates calibration by oleic acid. FIG. 6B illustrates calibration by linolenic acid;

DETAILED DESCRIPTION

A controllable and robust cell-free system has been developed that can achieve a remarkable production rate of fatty acids (FAs). The cell-free system has an advantage of maintaining the high FA production rate for a long period of time and does not require maintenance with restrictive and costly conditions associated with supporting live cell cultures. Thus, the present system is particularly suitable for efficient and economical industrial production.

Accordingly, in one aspect the present disclosure provides a composition for the production of fatty acids. The composition comprises an algal cell lysate, liquid medium, and an organic carbon source.

The term "fatty acid (FA)" as used herein refers to any carboxylic acid with an aliphatic tail. Most naturally occurring fatty acids have a chain of an even number of carbon atoms, such as from 4 to 28, and are usually derived from triglycerides or phospholipids. Short-chain fatty acids (SCFA) are fatty acids with aliphatic tails of fewer than 6 carbons (e.g., butyric acid). Medium-chain fatty acids (MCFA) are fatty acids with aliphatic tails of 6-12 carbons, which can form medium-chain triglycerides. Long-chain fatty acids (LCFA) are fatty acids with aliphatic tails 12 to 22 carbons. Very long chain fatty acids (VLCFA) are fatty acids with aliphatic tails longer than 22 carbons. FAs can be either unsaturated or saturated. Illustrative unsaturated FAs are set forth in Table 1, and illustrative saturated FAs are set forth in Table 2.

TABLE 2

Exemplary saturated FAs.

| Common name | Chemical structure | C:D |
|---|---|---|
| Caprylic acid | $CH_3(CH_2)_6COOH$ | 8:0 |
| Capric acid | $CH_3(CH_2)_8COOH$ | 10:0 |
| Lauric acid | $CH_3(CH_2)_{10}COOH$ | 12:0 |
| Myristic acid | $CH_3(CH_2)_{12}COOH$ | 14:0 |
| Palmitic acid | $CH_3(CH_2)_{14}COOH$ | 16:0 |
| Stearic acid | $CH_3(CH_2)_{16}COOH$ | 18:0 |
| Arachidic acid | $CH_3(CH_2)_{18}COOH$ | 20:0 |
| Behenic acid | $CH_3(CH_2)_{20}COOH$ | 22:0 |
| Lignoceric acid | $CH_3(CH_2)_{22}COOH$ | 24:0 |
| Cerotic acid | $CH_3(CH_2)_{24}COOH$ | 26:0 |

Figure 1:
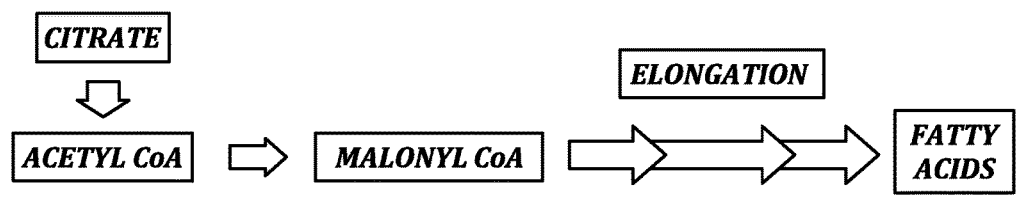
FIG. 1 schematically illustrates the role of citrate in the pathway for synthesizing FAs.

The compositions and methods of the present disclosure are useful for the production of any FA. In some embodiments, the multiple species of FA are produced with the compositions or methods described herein. Depending on the initial carbon substrate, Fas are biosynthesized according to a variety of known pathways. For example, FIG. 1 illustrates one pathway that incorporates citric acid as a carbon source.

The term "algae" as used herein refers to any organism with chlorophyll and, in other than unicellular algae, a thallus not differentiated into roots, stems, and leaves. The term encompasses organisms that are photoautotrophic, heterotrophic, or mixotrophic, and are typically found in freshwater and marine systems. The term "algae" includes macroalgae (such as seaweed) and microalgae. The term "microalgae" refers to any microscopic algae that are unicellular and simple multi-cellular microorganisms, including both prokaryotic microalgae, e.g., cyanobacteria (Chloroxybacteria), and eukaryotic microalgae, e.g., green algae (Chlorophyta), red algae (Rhodophyta), and diatoms (Bacillariophyta). Depending on the species, algae cell sizes can range from a few micrometers (µm) to a few hundreds of micrometers. The use of the term "algal" is used to indicate

TABLE 1

Exemplary unsaturated FAs.

| Common name | Chemical structure | $\Delta^x$ | CD |
|---|---|---|---|
| Myristoleic acid | $CH_3(CH_2)_3CH=CH(CH_2)_7COOH$ | cis-$\Delta^9$ | 14:1 |
| Palmitoleic acid | $CH_3(CH_2)_5CH=CH(CH_2)_7COOH$ | cis-$\Delta^9$ | 16:1 |
| Sapienic acid | $CH_3(CH_2)_8CH=CH(CH_2)_4COOH$ | cis-$\Delta^6$ | 16:1 |
| Oleic acid | $CH_3(CH_2)_7CH=CH(CH_2)_7COOH$ | cis-$\Delta^9$ | 18:1 |
| Elaidic acid | $CH_3(CH_2)_7CH=CH(CH_2)_7COOH$ | trans-$\Delta^9$ | 18:1 |
| Vaccenic acid | $CH_3(CH_2)_5CH=CH(CH_2)_9COOH$ | trans-$\Delta^{11}$ | 18:1 |
| Linoleic acid | $CH_3(CH_2)_4CH=CHCH_2CH=CH(CH_2)_7COOH$ | cis,cis-$\Delta^9,\Delta^{12}$ | 18:2 |
| Linoelaidic acid | $CH_3(CH_2)_4CH=CHCH_2CH=CH(CH_2)_7COOH$ | trans,trans-$\Delta^9,\Delta^{12}$ | 18:2 |
| α-Linolenic acid | $CH_3CH_2CH=CHCH_2CH=CHCH_2CH=CH(CH_2)_7COOH$ | cis,cis,cis-$\Delta^9,\Delta^{12},\Delta^{15}$ | 18:3 |
| Arachidonic acid | $CH_3(CH_2)4CH=CHCH_2CH=CHCH_2CH=CHCH_2CH=CH(CH_2)_3COOH$ | cis,cis,cis,cis-$\Delta^5,\Delta^8,\Delta^{11},\Delta^{14}$ | 20:4 |
| Eicosapentaenoic acid | $CH_3CH_2CH=CHCH_2CH=CHCH_2CH=CHCH_2CH=CHCH_2CH=CH(CH_2)_3COOH$ | cis,cis,cis,cis,cis-$\Delta^5,\Delta^8,\Delta^{11},\Delta^{14},\Delta^{17}$ | 20:5 |
| Erucic acid | $CH_3(CH_2)_7CH=CH(CH_2)_{11}COOH$ | cis-$\Delta^{13}$ | 22:1 |
| Docosahexaenoic acid | $CH_3CH_2CH=CHCH_2CH=CHCH_2CH=CHCH_2CH=CHCH_2CH=CHCH_2CH=CH(CH_2)_2COOH$ | cis,cis,cis,cis,cis,cis-$\Delta^4,\Delta^7,\Delta^{10},\Delta^{13},\Delta^{16},\Delta^{19}$ | 22:6 | being of or relating to algae. The term also relates to microalgae and thus encompasses the meaning of "microalgal." The term "algal composition" refers to any composition that comprises algae, and is not limited to the body of water or the culture in which the algae are cultivated. An algal composition can be an algal culture, a concentrated algal culture, or a dewatered mass of algae, and can be in a liquid, semi-solid, or solid form. A non-liquid algal composition can be described in terms of moisture level or percentage weight of the solids. An "algal culture" is an algal composition that comprises live algae.

In some embodiments, the algae used in connection with the present disclosure are microalgae. Non-limiting examples of microalgae that can be used with the methods and compositions of the disclosure are members of one of the following divisions: cyanobacteria (Cyanophyceae), green algae (Chlorophyceae), diatoms (Bacillariophyceae), yellow green algae (Xanthophyceae), golden algae (Chrysophyceae), red algae (Rhodophyceae), brown algae (Phaeophyceae), dinoflagellates (Dinophyceae), and "pico-plankton" (Prasinophyceae and Eustigmatophyceae). In some embodiments, the preferred algae for use in connection with the production of Fas are green algae (fresh water), Cyanobacteria, and Diotoms (Marine). In certain embodiments, the microalgae used with the methods of the disclosure are members of one of the following classes: Bacillariophyceae, Eustigmatophyceae, and Chrysophyceae. In certain embodiments, the microalgae used with the methods of the disclosure are members of one of the following genera: *Nannochloropsis, Chlorella, Dunaliella, Scenedesmus, Selenastrum, Oscillatoria, Phormidium, Spirulina, Amphora*, and *Ochromonas*.

Non-limiting examples of microalgae species that can be used in connection with the present disclosure include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis aff. galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricomutum, Phagus, Phormidium, Platymonas* sp., *Pleurochrysis camerae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii*, and *Viridiella fridericiana*.

In some embodiments, the algal lysate is derived from one or more algae cells from one of the following genera from the division Chlorophyta: *Botryococcus, Chlamydomonas, Chlorella, Chlorococcum, Dunaliella, Haematococcus, Monoraphidium, Muriellopsis, Neochloris, Oocystis, Pseudokirchneriella, Scenedesmus*, and *Tetraselmis*. In some embodiments, the algal lysate is derived from one or more algae cells from the genus *Botryococcus*. In one specific embodiment, the algal lysate is derived from the species *Botryococcus braunii*. In some embodiments, the algal lysate is derived from one or more diatom cells, such as from the genus *Cyclotella*. In some embodiments, the algal lysate is derived from one or more cyanobacteria cells, such as from the genus *Spirulina*.

In some embodiments, the algal cell lysate is derived from a monoculture of an algae species. In some embodiments, the algal cell lysate is derived from a culture of algae that is substantially a monoculture, which consists of over 50%, 60%, 70%, 80%, 90%, or 95% of the same algae species. In some embodiments, the algal cell lysate is derived from a heteroculture of multiple algae species, including a mixture of 2, 3, 4, 5, 10, 20, or more species in any proportion. In some embodiments, the various species are chosen for inclusion in the culture for known biochemical properties.

An "algal cell lysate" is an algal composition wherein the outer cell membranes of one or more algae cells therein has been ruptured or compromised in some way such that cytosol from the cells escapes the confines of the cell membrane. The algal cell lysate is preferably derived or generated from intact algal cells. In some embodiments, it is preferred that the algal cell lysate is derived or generated from a culture of living algal cells. Disruption, e.g., lysis, of the cell membrane can be accomplished according to any of a variety of known methods in the art, including mechanical lysis, sonic lysis, chemical lysis, and the like, or any combination thereof. Examples of mechanical lysis include use of a blender or compression in a homogenizer. Another example includes using a bead beater, where small beads are mixed with the algal composition and run in a rotor assembly, such as a blender. In some embodiments, the algal composition is first cooled or frozen. Sonic lysis can also be accomplished by inducing vibrations in the cells by the application of ultrasonic waves, according to methods known in the art. Chemical lysis can also be accomplished using detergents, various known chaotropic agents, and the like. Lysis can also be accomplished by simple freeze-thawing cycles.

In some embodiments, the lysate is a crude lysate, wherein nothing is further removed from the mixture after the cells have been lysed. In other embodiments, the lysate is further subjected to a separation procedure to remove various unlysed cells and cellular debris, such as membrane fragments, lipids, and various cellular organelles. Typically, such a separation procedure can be accomplished through ultra-centrifugation, which results in predictable bands of cellular debris and components that can be removed from the lysate.

As used herein, the term "liquid medium" refers to any liquid that comprises sufficient nutrients, co-factors, energy sources, and the like, that can facilitate the synthesis/elongation of Fas in an algal cell lysate. For example, as described in more detail below, the use of a typical algal cell culture medium known in the art, which is sufficient for facilitating the growth and division of living algal cells, was demonstrated as also being sufficient to support the production of Fas in a cell-free system incorporating algal lysate. As is demonstrated in more detail below, it has been demonstrated that a simple medium with reduced ingredients can sustain significant production of lipids in the cell-free system (see Tables 3 and 4). Thus, in some embodiments, the liquid medium can contain any one or more of the following chemical ingredients: $NaNO_3$, $CaCl_2$, $MgSO_4$, $K_2HPO_4$, $MnCl_2$, and Biotin. In some embodiments, the liquid medium can contain any one or more of the following chemical ingredients: $NaNO_3$, $CaCl_2$, $MgSO_4$, and $K_2HPO_4$.

As used herein, the term "carbon source" refers to any carbon-containing compound. In some embodiments, the carbon source is an organic carbon source (i.e., excluding carbon-containing sources that are historically not considered organic, such as oxides of carbon, cyanides, and allotropes of carbon). In some embodiments, the carbon source comprises a carbon-containing molecule that can serve as a substrate in a FA biosynthesis pathway. In some embodiments, the carbon source can comprise any amount of a single carbon-containing compound. In some embodiments, the carbon source is a mixture of two or more carbon-containing compounds in any amount or proportion. An exemplary, non-limiting list of carbon sources includes citrate, acetate, and carbohydrates, such as glucose, fructose, galactose, sucrose, maltose, lactose, and the like.

In another aspect, the disclosure provides a method for generating Fas. The method comprises providing an organic carbon source to an algal cell lysate, providing a liquid environment to the algal cell lysate, and maintaining the system for a sufficient time to permit elongation of fatty acids.

The algal cell lysate can be derived from algae cells as described above. In some embodiments, the algal cell lysate is substantially free of intact cell membranes. In some embodiments, the algal cell lysate is substantially free of living algal cells. For example, it is preferred that the algal cell lysate is derived from an algal culture where at least 50% of the algal cells have been lysed. In some embodiments, the application of the method provides a cell-free system for the production of Fas. In some embodiments, the application of the method provides a system free of intact cell membranes for the production of Fas.

The carbon source is described in more detail above. In some embodiments, the carbon source is provided to the algal cell lysate once. In some embodiments, the carbon source is provided to the algal cell lysate in a plurality of doses, i.e., intermittently, over time. As used herein, the term "intermittent" refers to a discontinuous provision of a carbon source where an aliquot of the carbon source is provided in multiple applications, each application separated by a period of time. The provision of each aliquot can be instantaneously added to the lysate (i.e., all at once), or can be provided at a particular rate over an extended period of time. In some embodiments, the carbon source is provided continuously over a period of time. In some embodiments, it is preferred that the carbon source be provided continuously at a controlled rate.

The carbon source can be provided over a period of time. The present disclosure demonstrates that the system described below is robust with the ability to continue production of Fas over a long period of time, such as beyond 100 days. Accordingly, the carbon source can be continuously or intermittently provided to the algal cell lysate for 1 or more days, such as 1, 2, 3, 4, 5, 10, 15, 20, 25, 30, 35, 40, 45, 50, 55, 60, 65, 70, 75, 80, 85, 90, 95, 100, 105, 110, 115, and 120, or more days, or any range therein until FA production has ceased or significantly slowed, or due to exhaustion of the system. The amount and rate of carbon source can be adjusted for factors, such as the volume and content (i.e., algae type) of the algal lysate.

The liquid environment comprises the liquid medium, as described above. The liquid environment comprises sufficient liquid medium to provide the necessary nutrients, co-factors, and the like, to support FA production. Additionally, the liquid environment provides sufficient volume to permit the proper mixing to facilitate distribution of the nutrients and components of the FA biosynthesis pathway.

In some embodiments, the method also comprises agitating the liquid environment (as mixed with the other components in the method) continuously or intermittently over time to facilitate mixing of the components.

In some embodiments, the method also comprises isolating the Fas according to techniques familiar in the art, such as fractional distillation, which requires extraction by organic solvent (such as chloroform and methanol) followed by esterification to make fatty acids become esters.

The method can be carried out in any appropriate container, including a cell culture container, a vat, or even an outdoor pond/pool.

As described below, it has been demonstrated that the system can efficiently produce lipids without requiring light input. Accordingly, the method can be carried out without regard to light or dark parameters.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below" and words of similar import, when used in this application, shall refer to this application as a whole and not to any particular portions of the application.

Disclosed are materials, compositions, and components that can be used for, can be used in conjunction with, can be used in preparation for, or are products of the disclosed methods and compositions. It is understood that, when combinations, subsets, interactions, groups, and the like, of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

The following is a description of an embodiment of the present invention using a lysate of *Botryococcus braunii* to produce a robust cell-free system capable of producing significant quantities of Fas for an extended period of time.

A large number of *B. braunii* ($10^4$ cells/ml) were obtained in a culture and subjected to lysis. Cells were lysed by using a bead beater system (Mini-Beadbeater-16; BioSpec, Bartlesville, Okla.) for 3 minutes. The lysis solution was centrifuged using an Eppendorf 5415D centrifuge (Eppendorf, Hauppauge, N.Y.) at 10,000×G for 3 minutes. The resulting supernatant was extracted to obtain a lysate free of intact cells or cell membrane fragments. The supernatant was mixed with an algal-cell growth medium (Modified Bold 3N Medium, UTEX, University of Texas at Austin, Tex.) to provide any required nutrients and cofactors for the elongation of Fas.

Citrate, in the form of sodium citrate tribasic dehydrate, was added to the cell-free system every 24 hours at a concentration of 2 mM (system volume). Citrate serves as a key factor for FA synthesis. It has long been known that citrate can be cleaved into Acetyl-CoA, which is the building block for FA synthesis. Enzymes present in the cell-free system facilitate the elongation of the FA chains. The elongation process typically stops when achieving Fas of 16 or 18 carbons. FIG. 1 shows a simple illustration of a pathway of FA synthesis in cells. It will be understood that in application, the citrate can be replaced by other sources of organic carbon, such as glucose and the like.

After initial mixing, the system was maintained in polystyrene cell culture containers. At this small scale, the liquid environment was continuously agitated using a shaker at medium speed. The solution appeared clear when first prepared. By 5 days, small white particles were visible in the solution, and by 12 days, the solution was noticeably opaque as a result of a large production of Fas (not shown).

Figure 2:
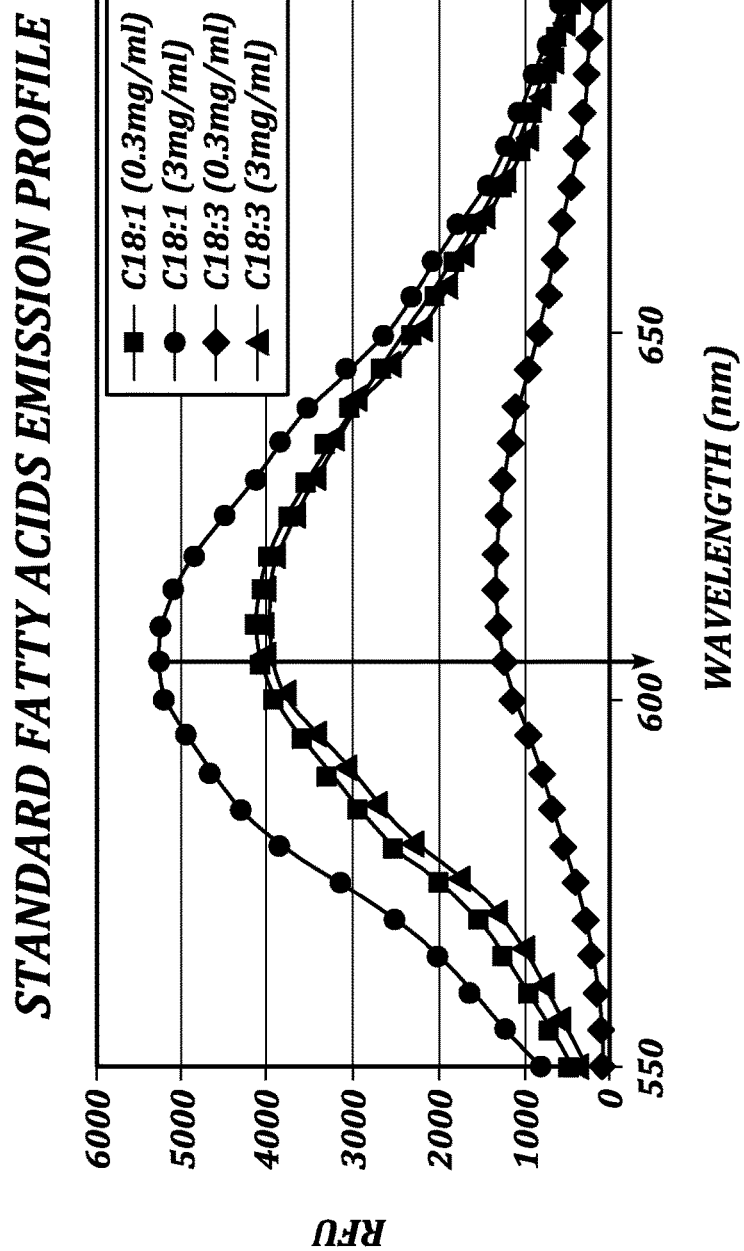
FIG. 2 graphically illustrates the red fluorescent emission profile of different standard fatty acids with different concentrations.
Figure 3A:
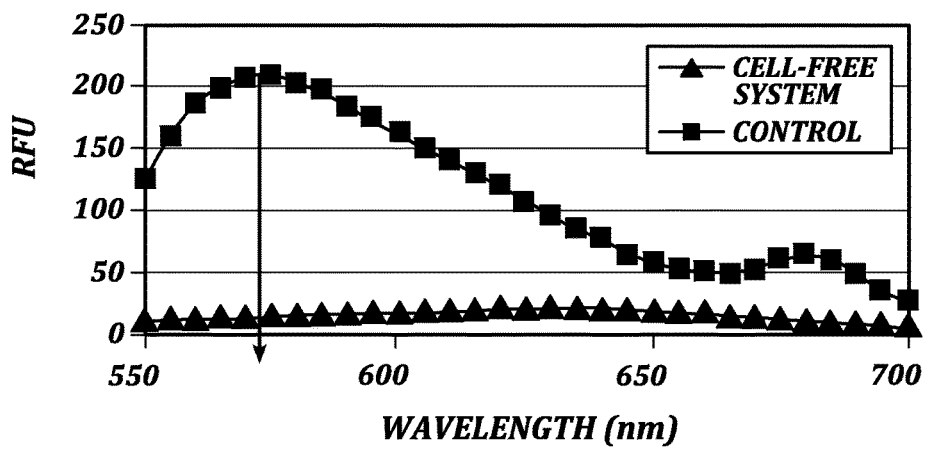
FIGS. 3A and 3B graphically illustrate the comparison of fatty acid production of algal cultures and the cell-free system at two time periods of incubation.

Nile Red, a fluorescent dye that binds to lipids and emits at red wavelengths under excitation, was used to detect the presence of Fas. Referring to FIG. 2, standard Fas demonstrated emission peaks within the range of 605 nm (see downward arrow) to 620 nm. Referring to FIG. 3A, at Day 5 the cell-free system demonstrated a relatively minor intensity in the 605 nm to 620 nm range (see arrow), as compared to the control *B. braunii* cell culture system. However, by 28 days, the intensity surprisingly increased 2,500 fold, indicating that the system had been producing a large amount of Fas. In stark contrast, the regular *B. braunii* cell culture system produced significantly lower FA levels. See FIG. 3B. These data demonstrate that over time the cell-free based system provided a robust generation of Fas with drastically higher efficiency than a live-cell culture system.

Figure 4A:
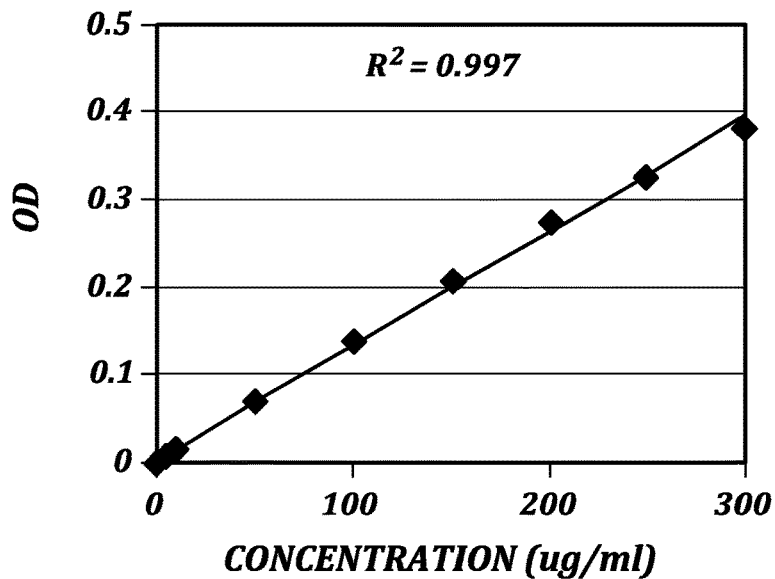
FIGS. 4A and 4B graphically illustrate the calibration of optical density (OD) by gradient concentrations of standard fatty acids.
Figure 4B:
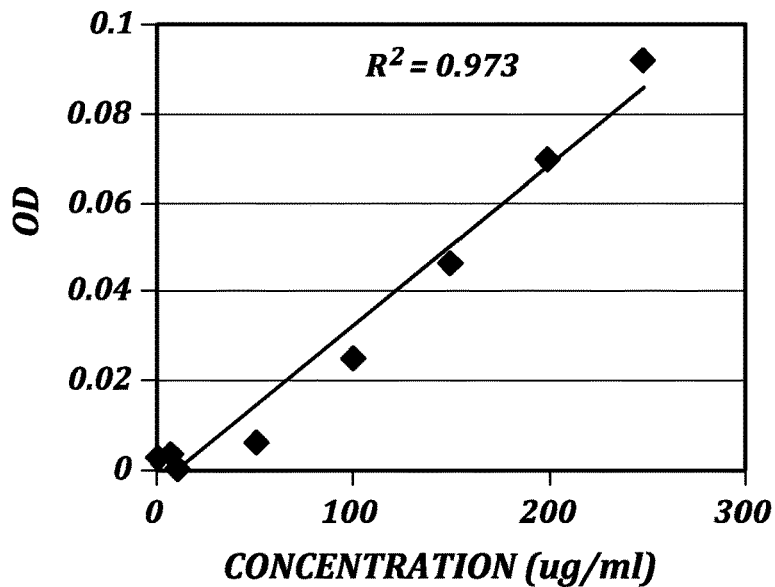
Figure 5:
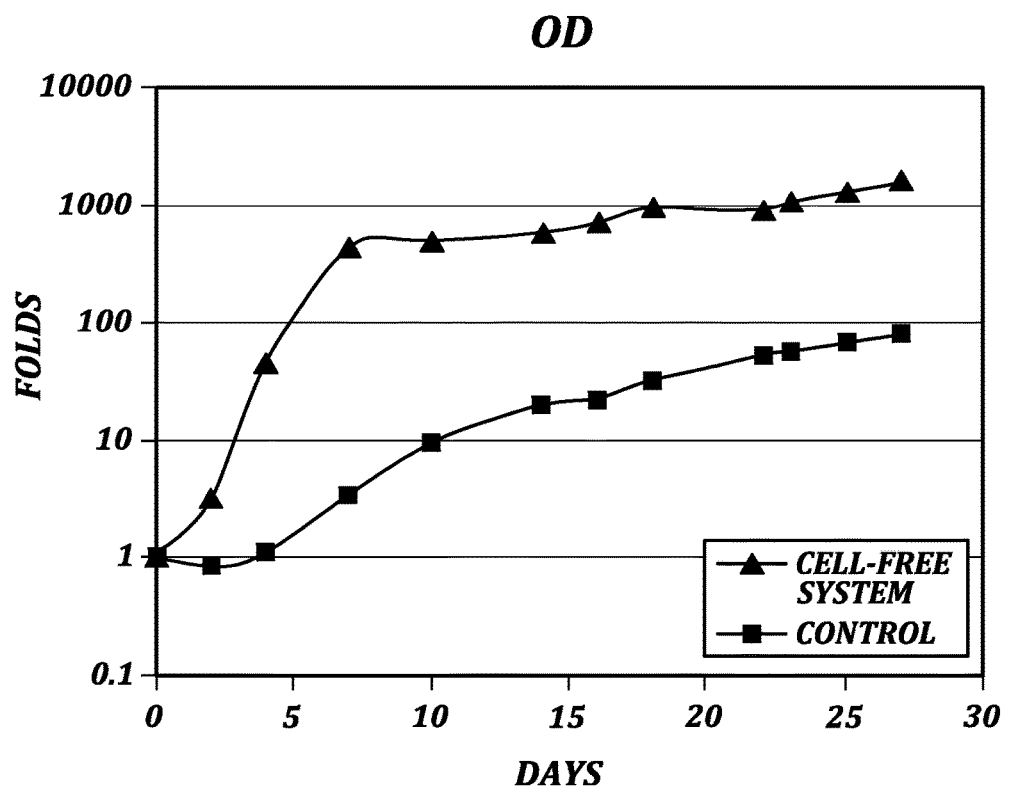
FIG. 5 graphically illustrates the optical density (OD) of samples from the cell-free system and a regular *B. braunii* culture system (indicated as "Control") over time.

The cell-free system was further assessed during maintenance to characterize FA production. By using Optical Density (OD), the particle numbers (such as, in this case, for FA particles) inside the solution were indirectly measured. As a preliminary matter, the relationship between OD and FA concentration was established. Specifically, FIGS. 4A and 4B illustrate a strong linear correlation between FA (i.e., C18:1 and C18:3, respectively) concentration and OD. As illustrated in FIG. 5, the particle numbers inside the cell-free system increased immediately and significantly within ten days. Even thereafter, the particle numbers continued to increase past 25 days.

Figure 6A:
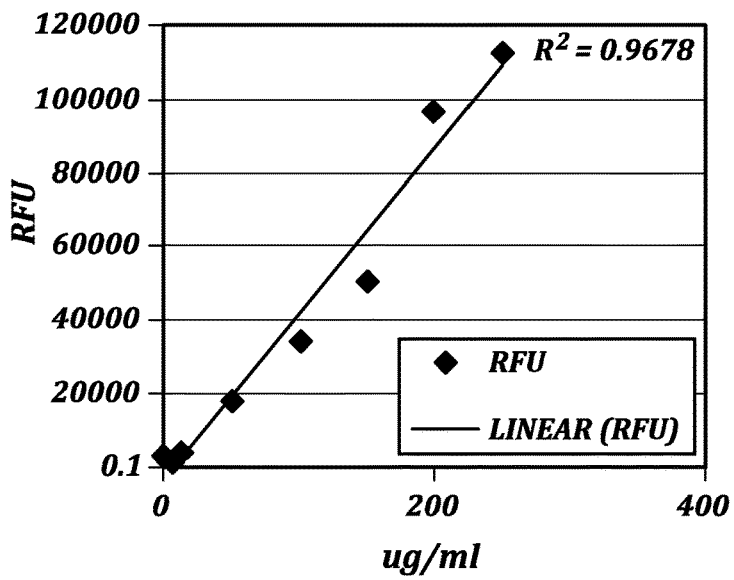
FIGS. 6A and 6B graphically illustrate the calibration of relative fluorescence units (RFU) by gradient concentrations of standard fatty acids.
Figure 6B:
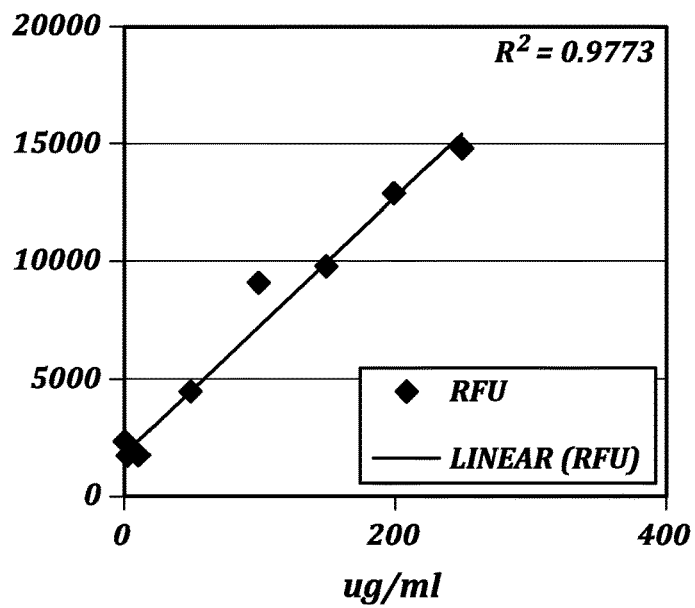
Figure 7:
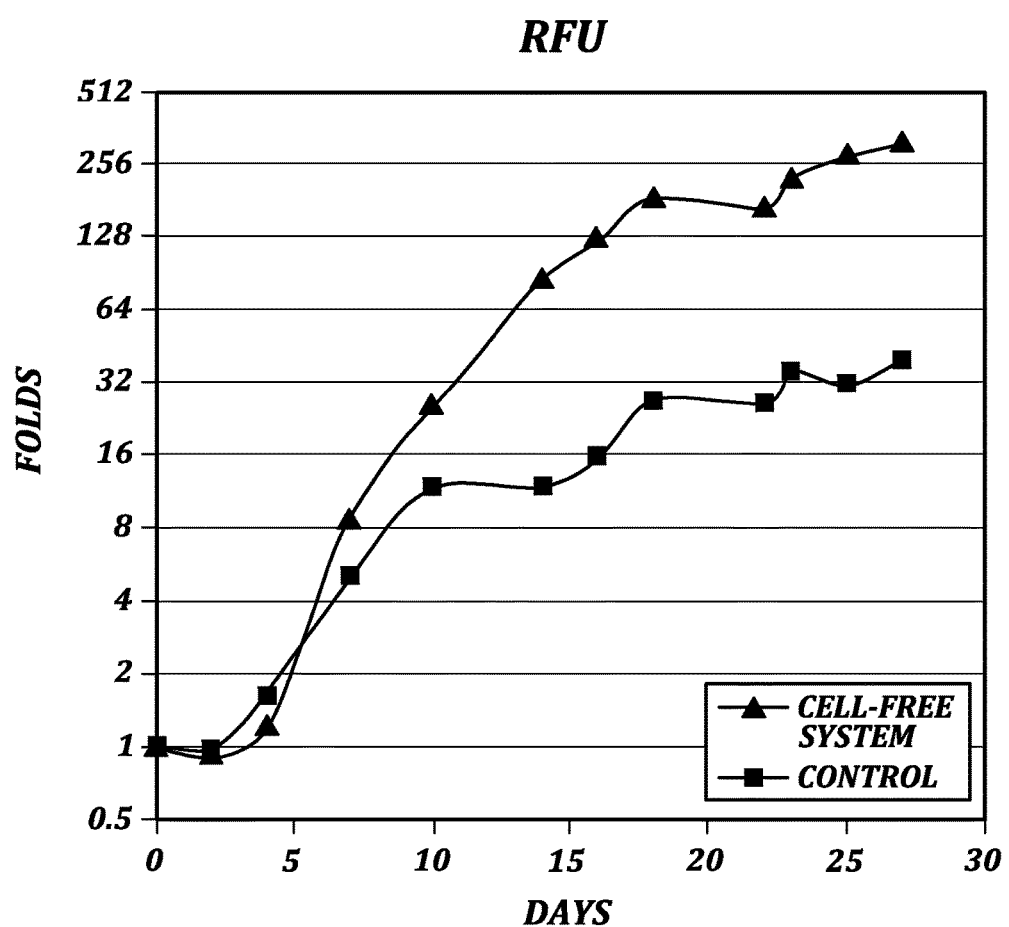
FIG. 7 graphically illustrates relative fluorescence units (RFU) of samples from the cell-free system and a regular *B. braunii* culture system (indicated as "Control") over time.

To analyze the production of Fas, curves in FIGS. 3A and 4B were used to calculate relative fluorescence units (RFU). Here, RFU was defined by taking the area under curve from 550 nm to 650 nm. As demonstrated in FIG. 6, a strong correlation exists between FA concentration and RFU. Referring to FIG. 7, a dramatic increase in RFU in the cell-free system was observed after Day 5, which indicates a dramatic increase of FA. RFU in the cell-free system exceeded that of regular cell culture system (Control) after one week. By Day 28, the cell-free system had FA levels that exceed the control cell culture by almost 10 times. Moreover, the ability to maintain the FA production rate for up to 28 days demonstrated that the cell-free system is robust.

Figure 8:
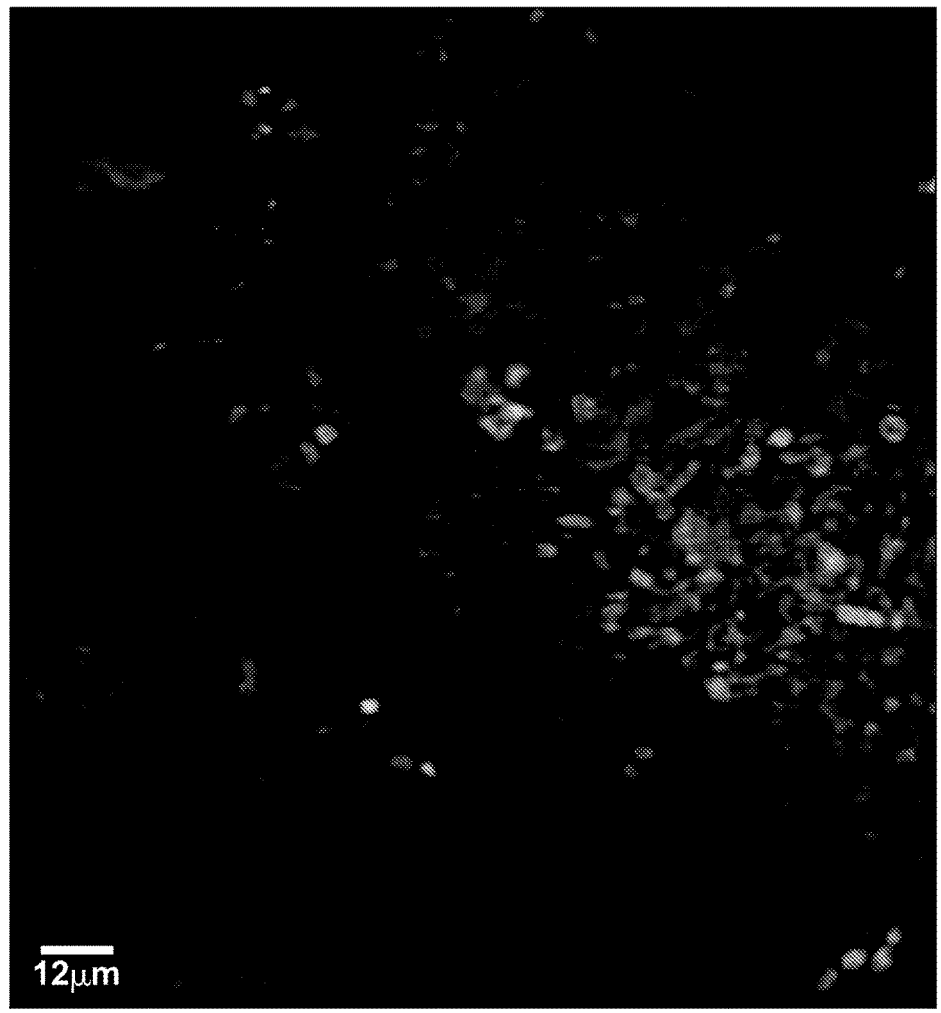
FIG. 8 is a confocal microscope photograph of a sample from the cell-free system, where the Nile Red stain binds to small particles and emits red fluorescence. The scale bar represents 12 μm.

The Nile Red dye was employed to visualize the FA particles in the cell-free system at Day 28. FIG. 8 illustrates that large quantities of small, red FA particles in the cell-free system were freely floating within the solution. This indicates that Fas were free in the cell-free solution after prolonged maintenance, which suggests the amenability of convenience harvesting and purification processes.

Figure 3B:
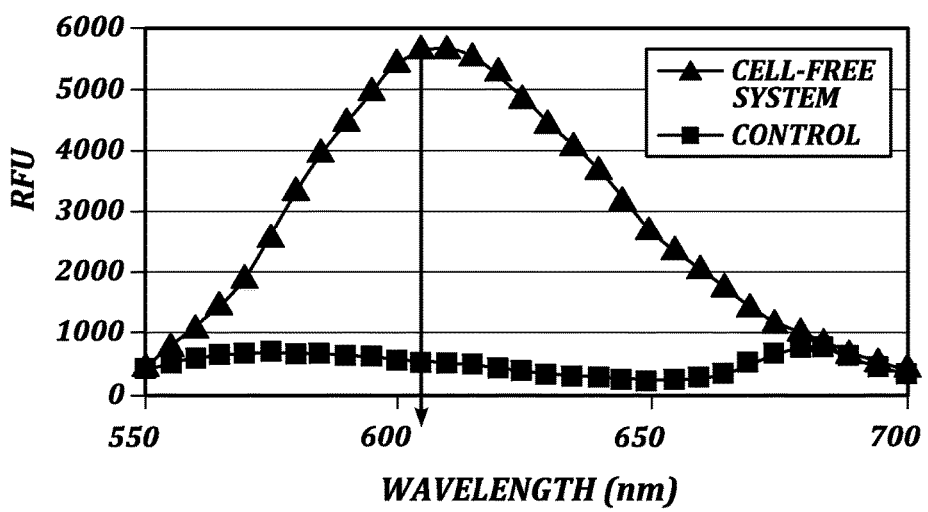

It is noted that the emission spectra of the Nile Red fluorescent method can indicate the fatty acids composition. At the beginning of the experiment, the emission profiles have two peaks, with a peak at 585±5 nm, representing lipid content, and another peak at 680 nm, caused by autofluorescence of chlorophyll (FIG. 3A). On Day 28, the sample with no added citrate still showed the two peaks, both of which increased over time, reflecting the increase in total number of cells and total amount of lipids (FIG. 3B). In contrast, the sample to which citrate was added continuously showed a shift in the lipid peak from 585±5 nm to about 610±5 nm. This peak shift usually started happening between Day 4 and Day 10 and thereafter would have the same general shape and only differ in peak value (FIG. 3B).

Cultures with continuous citrate addition showed a shift in the lipid peak of the emission spectra from 575 nm to the right, overshadowing the chlorophyll peak near 680 nm. The fluorescence properties of Nile Red (9-diethylamino-5H-benzo[\alpha]phenoxazine-5-one) are altered by the polarity of its immediate environment, due to a large change in dipole moment upon excitation. Depending on the hydrophobicity of the solvents, the peak of Nile Red fluorescence can vary 60 nm, shifting toward the red in more polar environments. Thus, systems continuously supplied with citrate appeared to become more polar environments, possibly due to the production of more polar lipids.

Thus, it is demonstrated that the cell-free system as described herein, including an algal cell lysate (e.g., *B. braunii* lysate), culture medium, and an organic carbon source, generated a large amount of Fas within a short time. Furthermore, the cell-free system produced significantly greater FA quantities over time than corresponding intact cell cultures. The cell-free system was robust, with the demonstrated high-rate of Fas continuing for up to about 30 days from the initiation of the system. Thus, the cell-free system shows great potential to be scaled up and applied to industrial production.

The following is a description of the further characterization of an embodiment of the present invention using a lysate of *Botryococcus braunii* to produce a robust cell-free system capable of producing significant quantities of Fas for an extended period of time.

As demonstrated above, a cell-free system using algal cell lysate, culture medium, and an organic carbon source generated a high rate of FA production for up to 30 days. The present study describes the additional characterization of such a system to demonstrate the robust production of Fas for a longer duration. Furthermore, the present study describes the effects of various factors including light and optimized culture components on the production of Fas by the system.

Figure 9:
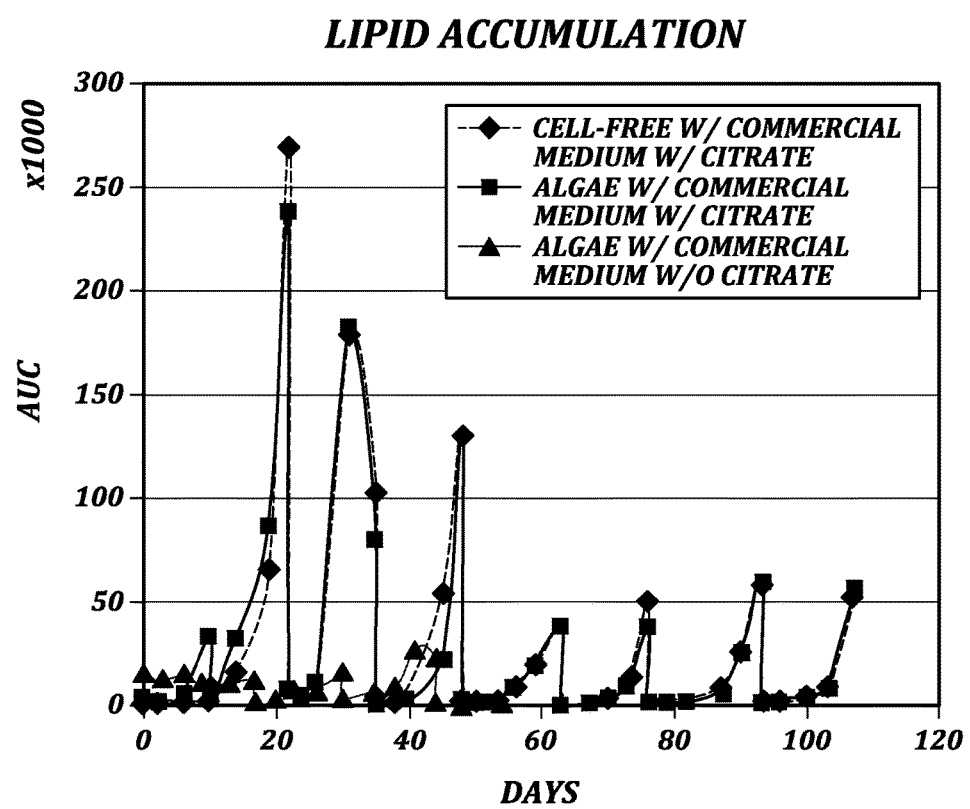
FIG. 9 graphically illustrates the lipid levels (AUC×1000) over time in continuous cell-free and cell cultures of *B. braunii* with periodic medium replacement. Diamonds indicate the lipid accumulation of cell-free cultures in commercial medium with citrate; squares indicate cell cultures in commercial medium with citrate; and triangles indicate cell cultures in commercial medium without citrate.
Figure 10:
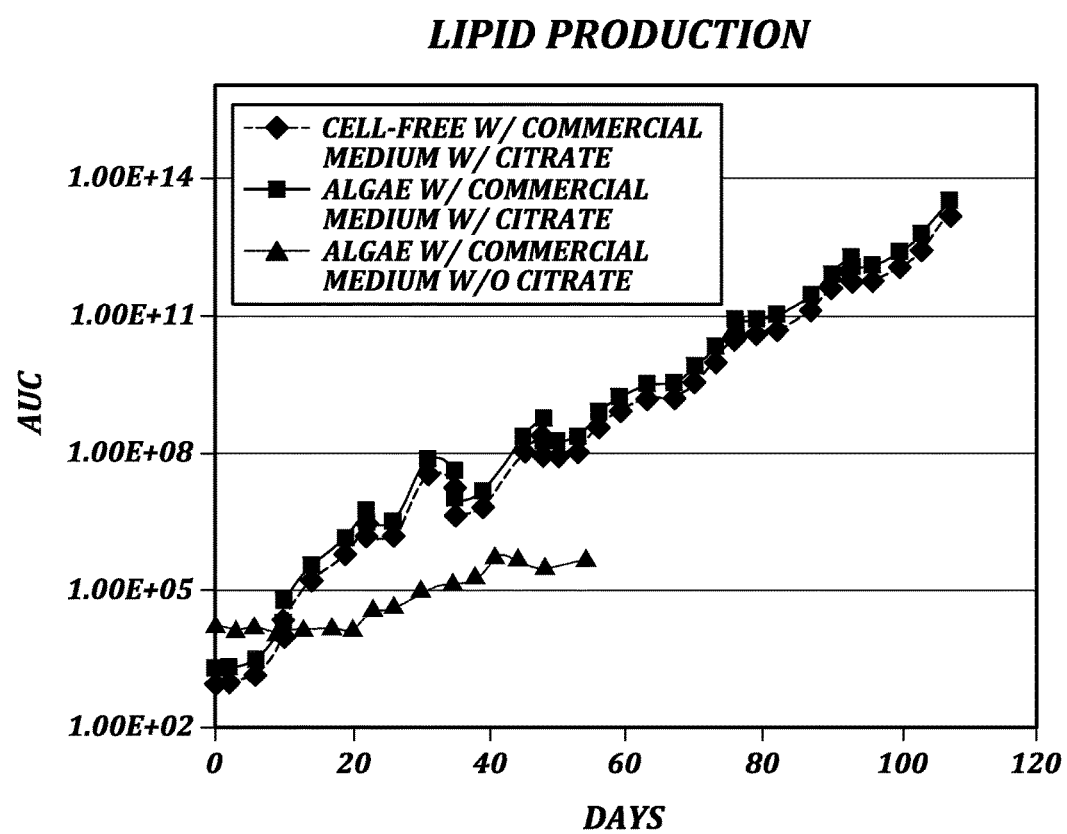
FIG. 10 graphically illustrates the accumulated lipid production in continuous cell-free and cell cultures of *B. braunii*. As in FIG. 9, diamonds indicate the lipid accumulation of cell-free cultures in commercial medium with citrate; squares indicate cell cultures in commercial medium with citrate; and triangles indicate cell cultures in commercial medium without citrate. Data are normalized to the original concentration at the beginning of the experiment and shown on a log scale.

Long term effects: Whole cell cultures of *Botryococcus braunii* as well as cell-free cultures from *B. braunii* were established as generally described above with citrate added at 2 mM every day and using commercial medium (Modified Bold 3N, from Culture Collection of Algae at the University of Texas at Austin (UTEX)). On Day 13, 1 ml of sample was taken and added to 19 ml of fresh medium. This procedure was repeated for a total of seven cycles. Lipid content was determined using the Nile Red dye method described above. Lipid content in the cell-free system showed a dramatic increase at every transfer to fresh medium (see FIG. 9). However, the increase tended to become smaller over time. Both culture systems reached the highest lipid contents at around Day 22, which is approximately 47 times the level at the beginning of the second cycle. Whole cell cultures with no citrate, used as a control, showed little lipid accumulate during the first 17 days, but subsequently showed a 4 to 5-fold increase. After the fourth transfer at 44 days, the lipid content remained constant. FIG. 10 illustrates the accumulated lipid production of the cultures over time, normalized to the original concentration.

Figure 11:
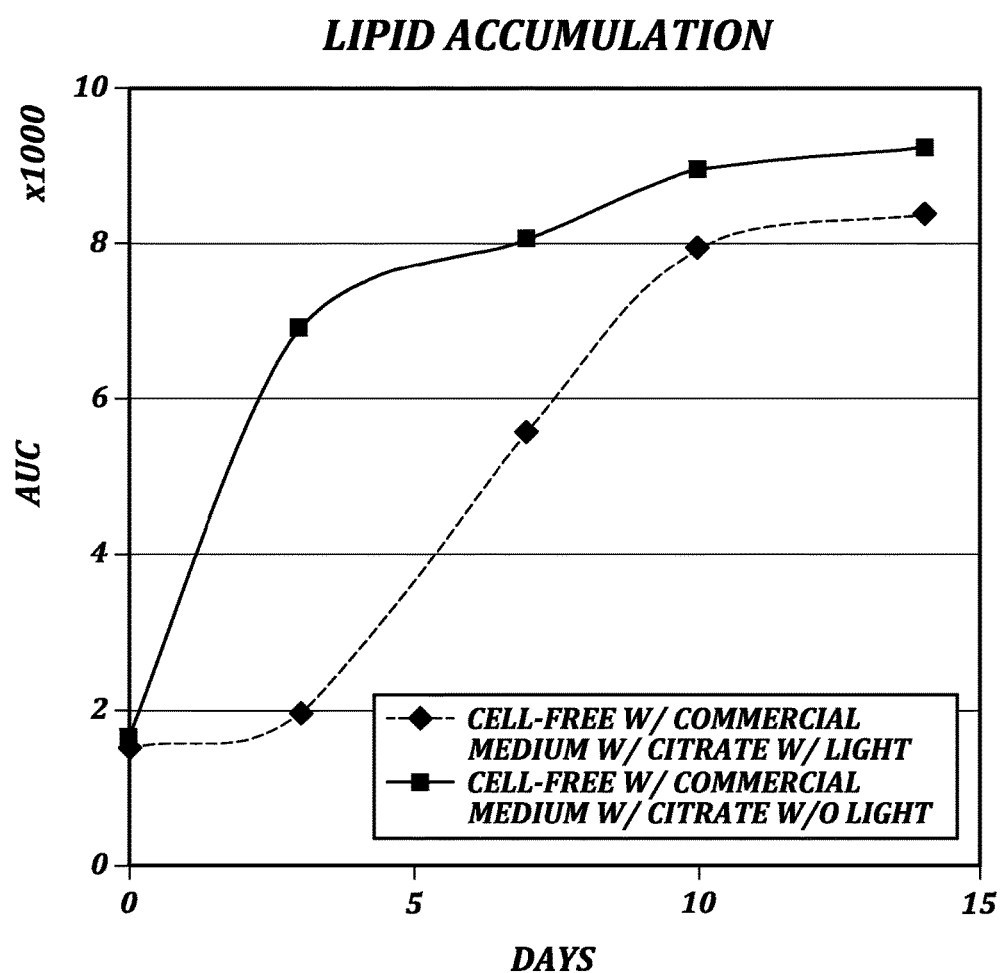
FIG. 11 graphically illustrates the lipid accumulation of the cell-free system over time with daily citrate supply, with or without light.

Effects of light: The effects of light were examined on lipid accumulation in the cell-free system with continuous citrate supply. Dark samples were covered with aluminum foil. Light samples were exposed to 100 $\mu$mol $m^{-2}$ $s^{-1}$ of light intensity provided by fluorescence lamp, 24 hours/day. It is noted that the specific intensity is not crucial. While intensity will affect the production of whole cells, it will not make the production increase over 20-50%. Excessive or insufficient intensity, however, will harm the production of whole cells. Nile Red emission spectra of dark and light samples showed similar patterns of lipid accumulation during a two-week period, but accumulation was delayed by four days in the dark samples (FIG. 11). In both cases, final lipid content was more than 7 times higher than initial lipid content, but final lipid content of the light samples was about 10% lower than content in the dark samples. These data establish that light is not a critical requirement for the cell-free production of lipids using the described system.

Profile of fatty acid production by *Botryococcus braunii*: Gas chromatography (GC) was used to examine the composition of the fatty acids in cultured *Botryococcus braunii*. In cultures with continuous citrate addition (with light), there were major peaks at 7.36, 12.23, 15.61, and 15.91 min retention times (not shown). Comparison to fatty acid standards indicated sample composition of 284 $\mu$g/ml tridecanoic acid, 542 $\mu$g/ml palmitic acid, 322 $\mu$g/ml stearic acid, and 4 $\mu$g/ml oleic acid. Another peak at 23.40 min was the internal control. In algae cultured under continuous citrate addition and under dark conditions, there were major peaks at 7.36, 12.23, 15.61, and 15.91 min (not shown), indicating 352 $\mu$g/ml tridecanoic acid, 493 $\mu$g/ml palmitic acid, 272 $\mu$g/ml stearic acid, and 11.3 $\mu$g/ml oleic acid. In contrast, algae cultures with no added citrate (under light conditions), which were concentrated threefold to increase the signal, showed major peaks at 7.35, 12.23, 15.60, 15.90, and 17.67 min, indicating original composition of 120 $\mu$g/ml tridecanoic acid, 205 $\mu$g/ml palmitic acid, 129 $\mu$g/ml stearic acid, 31 $\mu$g/ml oleic acid, and 12 $\mu$g/ml $\alpha$-linolenic acid.

Results of gas chromatography (GC) analyses indicated a change in fatty acid composition after continuous citrate supply. Compared to cultures with no citrate, whole cell cultures supplied with citrate (light and dark conditions) produced little linolenic acid (C18:3) and slightly less oleic acid (C18:1), but almost twice as much tridecylic acid (C13:0), palmitic acid (C16:0), and stearic acid (C18:0), which made up the majority of lipid content. Thus, daily citrate supply not only enhanced accumulation fatty acids, but altered the fatty acid composition. Nevertheless, the emission spectra of dark and light cultures were similar, and flow cytometry results showed that the composition of the fatty acids was also similar (not shown). Without light, cells produced about 10% less palmitic acid (C16:0), 15% less stearic acid (C18:0), and 20% more tridecylic acid (C13:0). As the latter accounts for only 25% of total lipids, and the majority of the lipids were palmitic acid and stearic acid, these changes could account for the changes in the emission spectra from the Nile Red dye method. These data indicate that a supply of organic carbon source can result in the enhanced production of multiple fatty acid species by the cellular pathways provided by the algal cells. Furthermore, the supply of the carbon source resulted in an altered profile of specific fatty acids produced by the algal cells. Because the cell-based system has very similar production behavior as cell-free systems derived from the same algal cells, the cell-free system would be expected to produce a similar profile shift with the same application of the carbon source.

Optimization of medium for lipid accumulation in the cell-free system: Determination of the optimal chemical composition of medium for lipid production by cell-free system generated by *Botryococcus braunii* culture was carried out using the "Feedback System Control (FSC)" technology. Briefly, the FSC experiment design uses a combination of a two-level factorial or fractional factorial design and a three-level orthogonal array to produce an orthogonal-array composite design. This method provides a trade-off between estimation efficiency and combination size economy. FSC has been previously used to determine optimal dosages for combinatorial drug therapy, and only a small number of iterations in the feedback loop were needed to find the optimal chemical combination in the current study.

Figure 12:
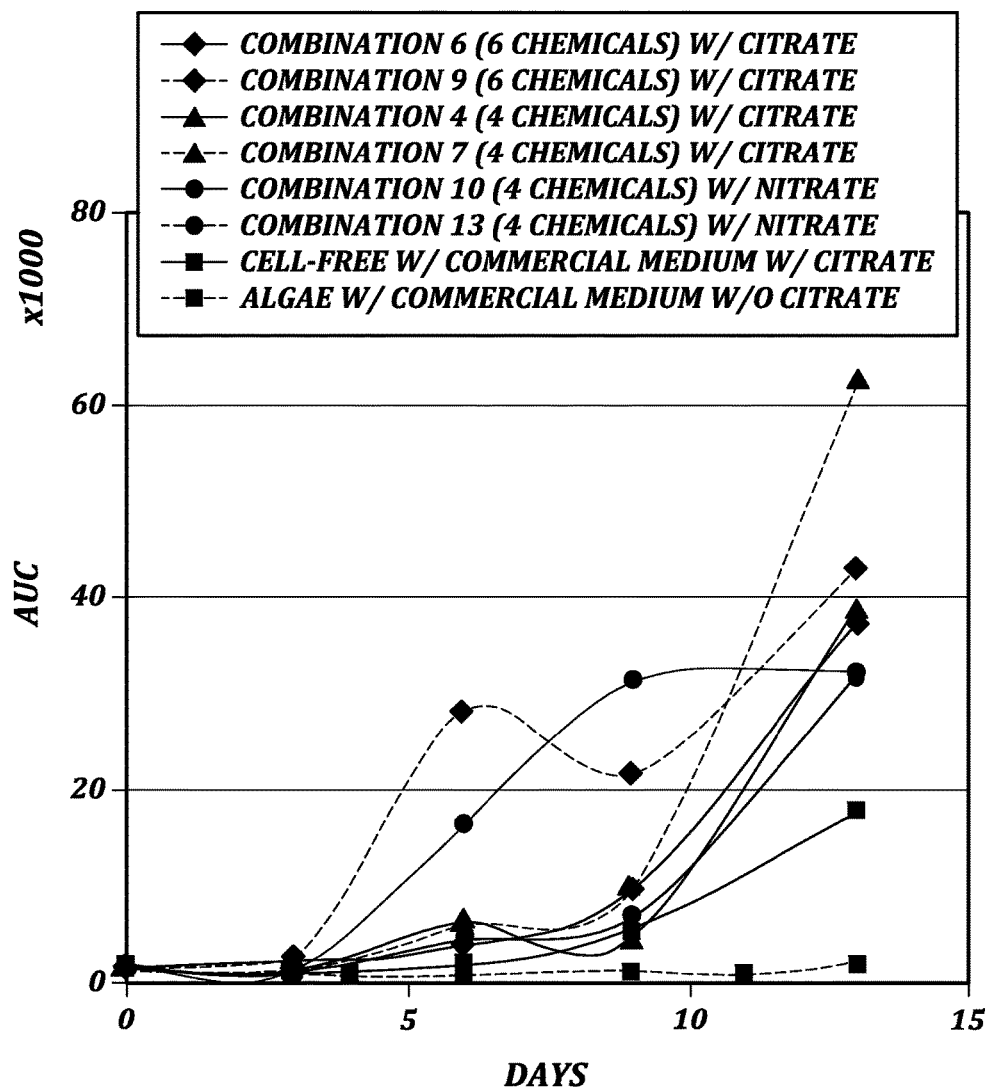
FIG. 12 graphically illustrates the lipid content of the cell-free system with citrate using different combinations of chemicals (see Table 4)

The level and real concentrations for the various chemical ingredients are shown in Table 3. The middle level (4) was the same used in the commercial medium. Level 1 was one order of magnitude lower than level 4, and level 7 was one order of magnitude higher than level 4. The cell-free system was able to produce high level of fatty acids with various combinations of only 6 or 4 chemicals in the optimized medium. See Table 4, which indicates the "level" of each ingredient as provided in Table 3. Comparing with the previously used commercial medium that is designed for algae cell, these new formulas enhanced the fatty acid production by another two or three times. See FIG. 12.

Conclusion: These data demonstrate the longer term production of lipids in the cell-free system described herein. The described cell-free system confers various benefits to the bio-synthesis of lipids. The cell-free system confers reduced costs compared to the systems requiring cultivation of live cells. The cell-free system confers reduced requirements for land (e.g., for outdoor space) or energy considering that light is no longer a crucial parameter. The cell-free system confers a greatly simplified culture medium. For example, significant and prolonged lipid production was established for four to six chemical supplements, instead of 16 or more chemicals in commercial media, which greatly reduced the cost of culture by an order of magnitude. The cell-free (e.g., lysed cell) system can maintain fatty acid production at a rate that is an order of magnitude higher than traditional algal culture for four months or more using an optimized culture medium and a continuous supply of organic carbon, such as citrate. Ultimately, this technology has potential for mass production of biofuels such as bio-diesel as a source of inexpensive, clean, and renewable energy.

TABLE 3

Levels and range of chemicals concentrations used in experiment.

| Chemicals | Symbol code | Levels and concentrations (g/L) | | | | | | |
|---|---|---|---|---|---|---|---|---|
| | | 1 | 2 | 3 | 4 | 5 | 6 | 7 |
| $NaNO_3$ | x1 | 0 | 0.162 | 0.348 | 0.75 | 1.62 | 3.48 | 7.5 |
| $CaCl_2 \cdot 2H_2O$ | x2 | 0 | 0.0025 | 0.005 | 0.025 | 0.054 | 0.116 | 0.25 |
| $MgSO_4 \cdot 7H_2O$ | x3 | 0 | 0.0162 | 0.0348 | 0.075 | 0.162 | 0.348 | 0.75 |
| $K_2HPO_4$ | x4 | 0 | 0.0162 | 0.0348 | 0.075 | 0.162 | 0.348 | 0.75 |
| $MnCl_2 \cdot 4H_2O$ | x5 | 0 | 2.91E−05 | 6.27E−05 | 1.35E−04 | 2.91E−04 | 6.27E−04 | 1.35E−03 |
| Biotin | x6 | 0 | 2.50E−06 | 5.00E−06 | 2.50E−05 | 5.39E−05 | 1.16E−04 | 2.50E−04 |

TABLE 4

Optimal combinations of chemicals tested for lipid accumulation.

| | $NaNO_3$ | $CaCl_2$ | $MgSO_4$ | $K_2HPO_4$ | $MnCl_2$ | Biotin |
|---|---|---|---|---|---|---|
| Combination 6 | 5 | 2 | 7 | 7 | 1 | 7 |
| Combination 9 | 4 | 1 | 5 | 7 | 1 | 7 |
| Combination 4 | 7 | 1 | 7 | 7 | — | — |
| Combination 7 | 5 | 1 | 7 | 4 | — | — |
| Combination 10 | 3 | 1 | 7 | 5 | — | — |
| Combination 13 | 4 | 1 | 7 | 4 | — | — |

Figure 13:
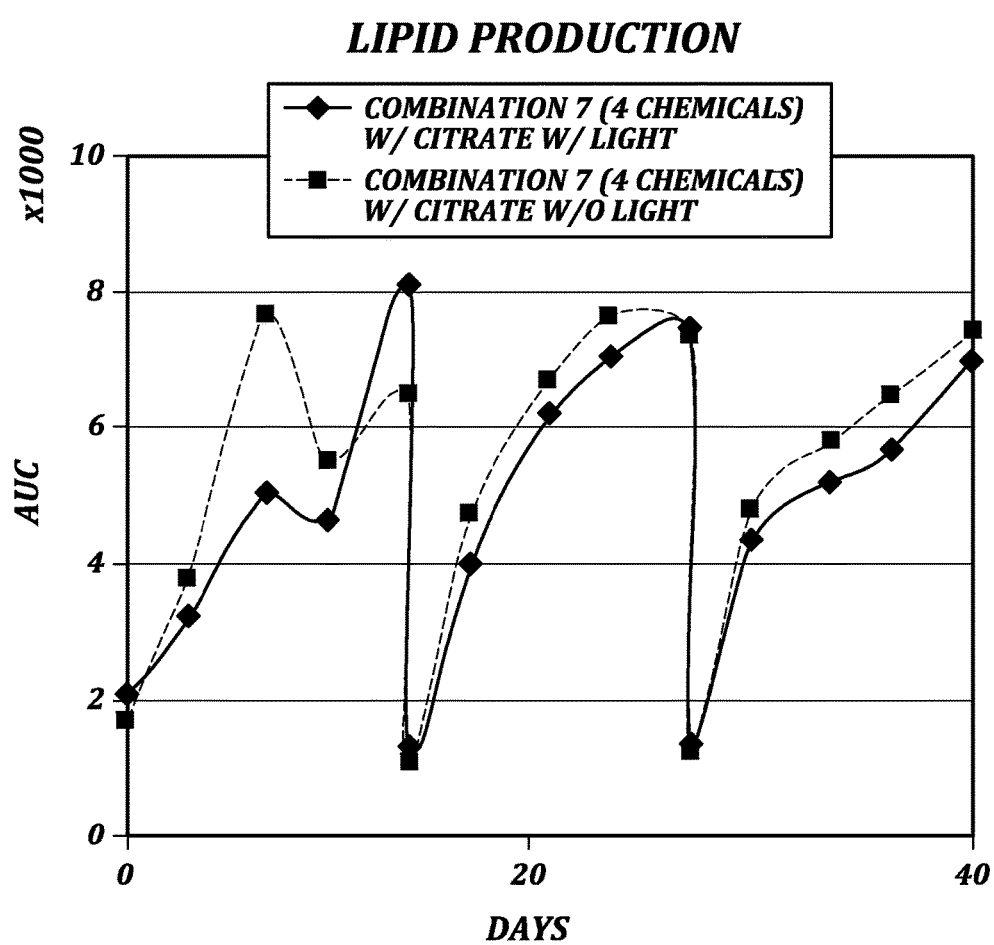
FIG. 13 graphically illustrates the lipid content in continuous cultures of the cell-free system with citrate, using the Combination 7 as the medium, and cultured in dark or light environments. Culture samples were transferred to fresh medium at two week intervals.
Figure 14:
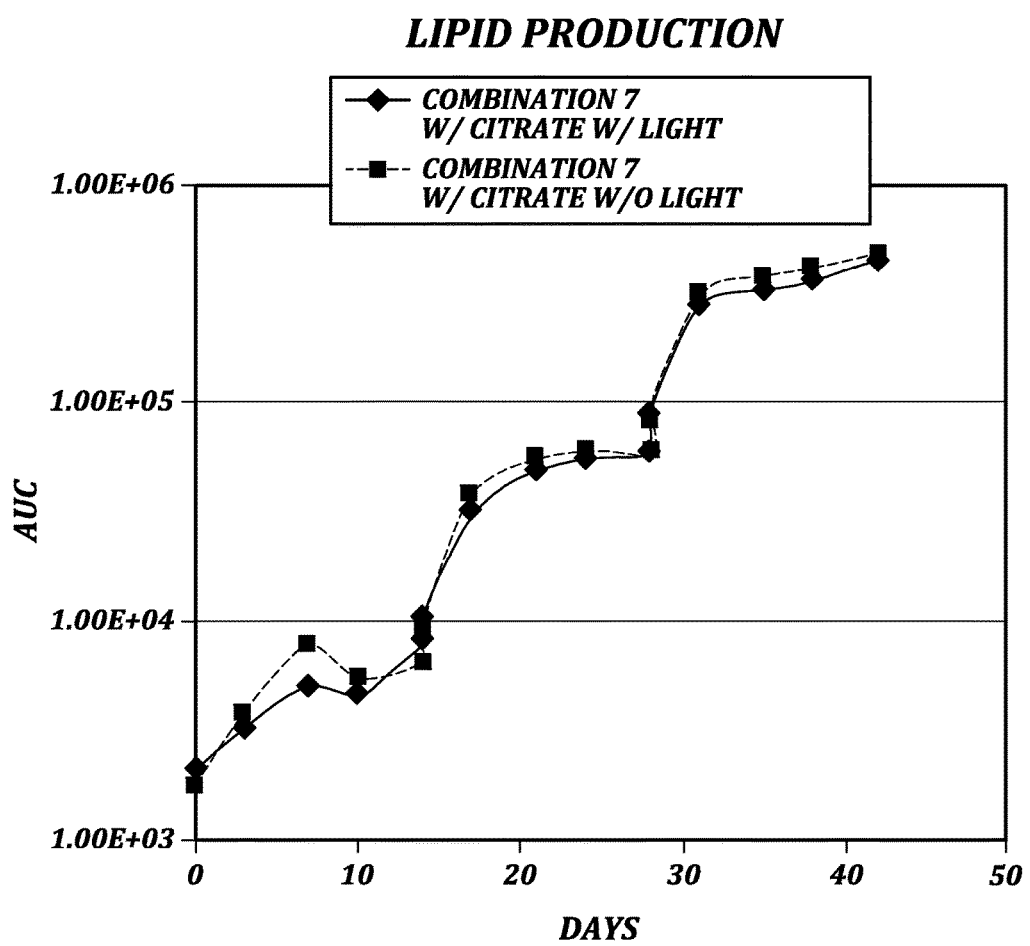
FIG. 14 graphically illustrates the lipid cumulative lipid production of the cell-free system with citrate, using the Combination 7 as the medium, and cultured in dark or light environments. The data is normalized to the original concentrations at the beginning of the experiment and presented in log scale.

The long-term ability of lipid accumulation by the cell-free system was established by using the most productive optimized medium, Combination 7 (see Table 4). 1 ml of sample was removed every two weeks and added to 19 ml of fresh medium. This procedure was repeated for 3 cycles, under dark and light conditions. Results of the most productive tests are shown in FIG. 13 and FIG. 14, respectively. The pattern of lipid accumulation in the optimized medium was similar to that in commercial medium: there was a rapid increase in lipid content, starting between Day 0 and Day 4; lipid content increased 7 to 8-fold in each cycle; and this pattern was maintained for 42 days. Lipid accumulation was independent of light: during the second and third cycles, lipid content was ~5% higher in the dark samples than in the light samples.

While the preferred embodiment of the invention has been illustrated and described, it will be appreciated that various changes can be made therein without departing from the spirit and scope of the invention.

The invention claimed is:

1. A method of generating fatty acids in a system, the method comprising:
   providing an organic carbon source to an algal cell lysate, wherein the organic carbon source is selected from citrate, acetate, glucose, fructose, galactose, sucrose, maltose, and lactose, and wherein the algal cell lysate is derived from one or more Chlorophyta algae cells from at least one of the following genera: *Botryococcus, Chlamydomonas, Chlorella, Chlorococcum, Dunaliella, Haematococcus, Monoraphidium, Muriellopsis, Neochloris, Oocystis, Pseudokirchneriella, Scenedesmus,* and *Tetraselmis,*
   providing a liquid environment to the algal cell lysate sufficient to permit mixing of the carbon source with the lysate, and
   maintaining the system for sufficient time to permit elongation of fatty acids.

2. The method of claim 1, wherein the one or more algal cells in the genus *Botryococcus* is *Botryococcus braunii*.

3. The method of claim 1, wherein the lysate is obtained by disrupting the cell membrane of one or more intact algae cells.

4. The method of claim 3, wherein the algae cell membrane is disrupted mechanically, sonically, or chemically.

5. The method of claim 4, wherein the algal cell lysate is substantially free of intact cell membrane.

6. The method of claim 1, wherein the organic carbon source is provided continuously or intermittently over time.

7. The method of claim 6, wherein the carbon source is provided over a period of at least 1 to 110 days.

8. The method of claim 1, wherein the liquid environment comprises sufficient nutrients to permit elongation of fatty acids chains.

9. The method of claim 1, wherein maintaining the system comprises agitating the liquid environment.

10. The method of claim 8, wherein the liquid environment is agitated continuously or intermittently over time.

11. The method of claim 1, further comprising isolating the fatty acids.

* * * * *